US009994890B1

(12) United States Patent
Epstein

(10) Patent No.: US 9,994,890 B1
(45) Date of Patent: Jun. 12, 2018

(54) METHODS OF NATURAL PRODUCT DRUG DISCOVERY

(71) Applicant: Northeastern University, Boston, MA (US)

(72) Inventor: Slava Epstein, Dedham, MA (US)

(73) Assignee: Northeastern University, Boston, MA (US)

( * ) Notice: Subject to any disclaimer, the term of this patent is extended or adjusted under 35 U.S.C. 154(b) by 280 days.

(21) Appl. No.: 13/770,532

(22) Filed: Feb. 19, 2013

Related U.S. Application Data

(60) Provisional application No. 61/600,206, filed on Feb. 17, 2012, provisional application No. 61/718,880, filed on Oct. 26, 2012.

(51) Int. Cl.
*C40B 30/06* (2006.01)
*C12Q 1/20* (2006.01)
*G01N 33/50* (2006.01)

(52) U.S. Cl.
CPC .............. *C12Q 1/20* (2013.01); *G01N 33/502* (2013.01); *C40B 30/06* (2013.01)

(58) Field of Classification Search
None
See application file for complete search history.

(56) References Cited

U.S. PATENT DOCUMENTS

2003/0068808 A1    4/2003    Nicolaides et al.

OTHER PUBLICATIONS

Merchant (Jun. 2011) Thesis the University of British Columbia pp. 1 to 183.*
Geng et al. (Jan. 11, 2008) Applied and Environmental Microbiology vol. 74 pp. 1535 to 1545.*
Martin-Galiano and de la Campa, "High-Efficiency Generation of Antibiotic-Resistant Strains of Streptococcus Pneumoniae by PCR and Transformation," Antimicrob Agents Chemother, vol. 47(4), pp. 1257-1261 (2003).
Tanyeri and Kennedy, "Detecting Single Bacterial Cells through Optical Resonances in Microdroplets," Sens Lett., vol. 6(2), pp. 326-329 (2008).
Nascimento et al. Antibacterial Activity of Plant Extracts and Phytochemicals on Antibiotic Resistant Bacteria. Brazilian Journal of Microbiology (2000) 31:247-256.
Saadoun et al. The Streptomyces flora of Badia region of Jordan and its potential as a source of antibiotics active against antibiotic-resistant bacteria. Journal of Arid Environments (2003) 53:365-371.
Bitzer et al. Accelerated Dereplication of Natural Products, Supported by Reference Libraries. Chimia 61 (2007) 332-338.

* cited by examiner

*Primary Examiner* — Christian C Boesen
(74) *Attorney, Agent, or Firm* — Posternak Blankstein & Lund LLP

(57) ABSTRACT

Disclosed are methods of identifying compounds that suppress the growth of target cells. In certain embodiments, the methods comprise providing a panel of target cells and the panel of target cells comprises a plurality of populations of target cells. Each population comprises cells that are resistant to one or more compounds known to suppress the growth of cells sensitive to the one or more compounds. Each population of target cells grows in the presence of a candidate compound and a determination of whether the candidate compound suppresses the growth of one or more populations of target cells.

30 Claims, 2 Drawing Sheets

| | | Resistant to: | | | | | | | | | |
|---|---|---|---|---|---|---|---|---|---|---|---|
| | | A | B | C | D | E | F | G | H | I | J |
| Antibiotic Added | A | ▓ | x | x | x | x | x | x | x | x | x |
| | B | x | ▓ | x | x | x | x | x | x | x | x |
| | C | x | x | ▓ | x | x | x | x | x | x | x |
| | D | x | x | x | ▓ | x | x | x | x | x | x |
| | E | x | x | x | x | ▓ | x | x | x | x | x |
| | F | x | x | x | x | x | ▓ | x | x | x | x |
| | G | x | x | x | x | x | x | ▓ | x | x | x |
| | H | x | x | x | x | x | x | x | ▓ | x | x |
| | I | x | x | x | x | x | x | x | x | ▓ | x |
| | J | x | x | x | x | x | x | x | x | x | ▓ |
| | linezolid | x | x | x | x | x | x | x | x | x | x |

Legend:

x       inhibition growth

Figure 2.

METHODS OF NATURAL PRODUCT DRUG DISCOVERY

CROSS-REFERENCE TO RELATED APPLICATION

This application claims the benefit of priority of U.S. Provisional Application Nos. 61/600,206, entitled "Method and Device for Drug Discovery", and 61/718,880, entitled "Novel Methods of Natural Product Drug Discovery", filed Feb. 17, 2012 and Oct. 26, 2012, respectively, the contents of which are incorporated herein.

FIELD OF THE INVENTION

The present invention relates, in part, to methods of identifying new sources of compounds that have a desired property, e.g., antimicrobial, anti-inflammatory, and anti-cancer compounds.

BACKGROUND

It is well known that current methods of drug discovery share one critical bottleneck: rediscovery of known, previously identified biological active compounds is prohibitively expensive. This makes the process of discovering novel compounds impractical.

For example, the standard manner in which new antibiotics are discovered involves overlaying a culture of a test strain of bacteria with a culture of a suspected producer of an antibiotic and then observing the culture for zones of inhibition. While this allows for the detection of antimicrobial activity, it does not provide any information as to the chemical nature of the activity leading to the inhibition of growth. Tracing, isolating, and identifying the source molecule of the activity requires then a substantial effort of natural product chemistry. Taking antibiotics as an example, it has been estimated that it may take up to $10^8$ microbial isolates to discover a novel useful antimicrobial.

While growing this number of isolates is feasible, de-replicating the antimicrobial compounds they produce, rediscovering in the process many or all of the antimicrobials so far described is far beyond the capabilities of today's analytical chemistry. As a result, natural product discovery divisions in big pharmaceutical companies have been closed down. In the meantime, the pipeline of novel antibiotics has dried up, and the need for them became urgent and critical.

New drug compounds are currently discovered by overlaying a source of unknown compounds over a test culture and observing the test culture for changes in growth or particular cellular activities. For example, the standard manner in which new antibiotics are discovered involves overlaying a culture of a test strain of bacteria with a culture of a suspected producer of an antibiotic and then observing the culture for zones of inhibition. While this allows for the detection of antimicrobial activity, it does not provide any information as to the chemical nature of the activity leading to the inhibition of growth. Tracing, isolating, and identifying the source molecule of the activity requires then a substantial effort of natural product chemistry. The process is similar for compounds having other desired properties, such as the suppression of growth or killing of cancer cells, and the modulation and manipulation of inflammatory pathways. Thus, discovery of chemically novel compounds having important properties for the treatment of disease causes researchers to rediscover some or all of the known compounds, making this process commercially impractical.

Thus, there remains a need in the art for rapid and efficient methods of screening unknown compounds for antimicrobial, anti-inflammatory, and/or anti-cancer properties. The inventions disclosed herein are likely to dramatically increase the speed of novel compound discovery, radically transforming today's methods of drug discovery.

SUMMARY OF THE INVENTION

This disclosure describes an entirely new concept for drug discovery via an efficient dereplication of known bioactive compounds. The principal novelty of the method and the tool is that dereplication of known compounds is achieved in one simple biological test as opposed to slow and expensive analytical chemistry methods that must be applied sequentially. This disclosure offers a new methodology for drug discovery, methodology that is radically different from the one traditionally employed in the field.

Other objects, features and advantages of the present invention will become apparent from the following detailed description and the claims. It should be understood, however, that the detailed description and examples, while indicating specific embodiments of the invention, are given by way of illustration only and are not intended to be limiting. Additionally, in light of the detailed description, it is contemplated that changes and modifications within the spirit and scope of the claimed invention will become apparent to those skilled in the art.

Aspects of the disclosed methods relate to identifying compounds that suppress the growth of target cells. The methods comprise providing a panel of target cells, wherein the panel of target cells comprises a plurality of populations of target cells. Furthermore, each population comprises cells that are resistant to one or more compounds known to suppress the growth of cells sensitive to the one or more compounds. The methods comprise growing each population of target cells in the presence of a candidate compound and determining whether the candidate compound suppresses the growth of one or more populations of target cells. The methods also entail selecting the candidate compound that suppresses the growth of all populations of target cells in the panel.

In certain embodiments, each population of target cells is a strain of bacteria. In particular embodiments, each population of target cells is a fungal strain. In more particular embodiments, each population of target cells is a *Saccharomyces cerevisiae* strain. In other particular embodiments, each population of *Saccharomyces cerevisiae* strains is resistant to one or more compounds known to suppress the growth of *Saccharomyces cerevisiae* strains sensitive to the one or more compounds.

In certain embodiments, each population of target cells is a *Schizosaccharomyces pombe* strain. In some embodiments, each population of *Schizosaccharomyces pombe* strains is resistant to one or more compounds known to suppress the growth of *Schizosaccharomyces pombe* strains sensitive to the one or more compounds. In other embodiments, each population of target cells is an *Escherichia coli* strain.

In particular embodiments, each population of *Escherichia coli* strains is resistant to one or more compounds known to suppress the growth of *Escherichia coli* strains sensitive to the one or more compounds. In some embodiments, the one or more compounds are antibiotics. In some embodiments, the one or more antimicrobial compounds are anti-fungal agents.

In some embodiments, the methods further comprise contacting the plurality of populations of target cells with a candidate compound comprises contacting the plurality of populations with an extract from a bacterial organism, an extract from an invertebrate organism, an extract from a fungal organism, or an extract from a plant tissue. In other embodiments, the methods further comprise contacting the plurality of populations of target cells with a candidate compound comprises contacting the plurality of populations with a candidate compound isolated from a bacterial organism, a fungal organism, an invertebrate organism, or a plant tissue. In other embodiments, the methods further comprise contacting the plurality of populations of target cells with a candidate compound comprises contacting the plurality of populations with a candidate compound isolated from a bacterial organism, a fungal organism, an invertebrate organism, or a plant tissue.

In certain embodiments, the target cells are cancer cells. In particular embodiments, each population of cancer cells is resistant to one or more compounds known to suppress the growth of cancer cells sensitive to the one or more compounds.

In still other embodiments, the methods further comprise contacting the plurality of populations of target cells with a candidate compound comprises contacting the plurality of populations with an extract from a bacterial organism, an extract from a fungal organism, an extract from an invertebrate organism, or an extract from a plant tissue.

In certain embodiments, the target cells are cells that mediate inflammation. In still other embodiments, each population of cells that mediate inflammation is resistant to one or more compounds known to suppress the growth of cells that mediate inflammation.

In particular embodiments, the methods further comprise contacting the plurality of populations of target cells with a candidate compound comprises contacting the plurality of populations with a candidate compound isolated from a bacterial organism, a fungal organism, an invertebrate organism, or a plant tissue. In more particular embodiments, the methods further comprise contacting the plurality of populations of target cells with a candidate compound comprises contacting the plurality of populations with an extract from a bacterial organism, an extract from a fungal organism, an extract from an invertebrate organism, or an extract from a plant tissue.

In some embodiments, the candidate compounds kill each of the plurality of populations of target cells. In other embodiments, the candidate compound exhibits anti-cancer activity. In still other embodiments, the candidate compound exhibits anti-inflammatory activity.

In certain embodiments, the plurality of populations of target cells is provided in a multiwell plate. In some embodiments, the panel comprises at least 100 populations of target cells.

In particular embodiments, the candidate compound is obtained from a microbial spent medium or a chemical library.

In certain embodiments, the cells that mediate inflammation are selected from the group consisting of granulocytes, mast cells, basophils, T-cells, natural killer cells, leukocytes, and macrophages. In some embodiments, the determining whether the candidate compound suppresses the growth of one or more populations of target cells is carried out using spectrophotometry, flow cytometry, luminosity assay, colorimetric assay, or fluorescence assay.

DESCRIPTION OF THE FIGURES

The following figures are presented for the purpose of illustration only, and are not intended to be limiting:

FIG. 2 is a chart showing the optical density ("OD") of cultures containing bacteria grown in either an antibiotic or without antibiotic (w/o AB).

DETAILED DESCRIPTION OF THE INVENTION

1. Definitions

Figure 1:
FIG. 1 is a chart showing the cell growth of bacterial strains resistant to one or more antibiotics. Cell growth in an antibiotic is designated as a gray box. The absence of cell growth is designated with an "x."

As used herein, the following terms will have the following meanings.

The terms "about" or "approximately" are defined as being close to as understood by one of ordinary skill in the art, and in one non-limiting embodiment the terms are defined to be within 20%, preferably within 10%, more preferably within 5%, still more preferably 1%, and most preferably within 0.5%.

The terms "inhibiting" or "reducing" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The word "a" or "an" when used in conjunction with the term "comprising" in the claims and/or the specification may mean "one," but it is also consistent with the meaning of "one or more," "at least one," and "one or more than one."

The term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

As used herein, the term "strain" means a group of cells within a species or genus that exhibits a particular quality not exhibited in other members of the same species or genus. For example, a strain of E. coli cells that are resistant to ampicillin would be a strain of E. coli because other members of the species of E. coli are not resistant to ampicillin.

2. Methods Of Identifying Compounds

The present disclosure provides methods and devices for the efficient identification of new compounds that exhibit the ability to inhibit or suppress the growth of target cells. In certain instances, the target cells are killed by the new compounds. Thus, the identification of the novel chemical entity can be achieved via inexpensive biological dereplication, and in one step, bypassing the need for prohibitively expensive chemical dereplication.

Aspects of the disclosed methods comprise providing a panel of target cells in which the panel of target cells comprises a plurality of populations of target cells. A panel of target cells can be provided as a microtiter plate including cells such that the microtiter plate allows for monitoring the growth of cells. The target cells can be placed into wells of the microtiter plate with a medium sufficient to allow growth of the target cells. Microtiter plates having 96, 384, and 1536 are commercially available from e.g. Eppendorf AG (Hamburg, DE). A panel can also be a microfluidics plate capable of holding multiple samples for analysis. For example, CellASIC Corp. provides the ONIX™ Microfluidic Plates product, which includes a 96-well footprint (CellASIC Corp., Hayward, Calif.). The panel can also include growing cells in any way that allows for discrimination between different strains of cells, as well as differential analysis of the effects of a compound on each strain of target cells.

In aspects disclosed herein, the panel of target cells can be provided in a miniaturized version of standard microtiter plate but containing thousands of wells. In these aspects, each well houses a monoculture of one microbial strain resistant to one or more of the known antibiotics such that the entire plate contains monocultures resistant to all or most of the known antibiotics. In certain embodiments, the test source material is applied to all wells. Such a panel can be built using e.g. microfluidic technologies and the examination of wells can be accomplished visually under a microscope or automatically in a plate reader.

The methods also comprise using strains of target cells that are resistant to one or more compounds known to suppress the growth of cells sensitive to the one or more compounds. Each strain can be resistant to one known compound or each strain can be resistant to a combination of known compounds. For example, a strain of *E. coli* can be resistant to one antibiotic or resistant to several antibiotics.

Regarding the methods disclosed herein, some embodiments provide for identifying compounds that suppress the growth of target cells. In some aspects of the invention, each population of target cells is a fungal strain. Each population of target cells can be a *Saccharomyces cerevisiae* or a *Schizosaccharomyces pombe* strain. In such embodiments, the *Saccharomyces cerevisiae* strains can be resistant to one or more compounds known to suppress the growth of *Saccharomyces cerevisiae* strains sensitive to the one or more compounds. In yet other embodiments, the *Schizosaccharomyces pombe* strains are resistant to one or more compounds known to suppress the growth of *Schizosaccharomyces pombe* strains sensitive to the one or more compounds. The disclosed methods can be used with any fungal strain. A non-limiting list of exemplary fungal cells include *Aspergillus terreus*, *Saccharomyces cerevisaie*, *Schizosaccharomyces pombe*, *Saccharomyces boulardii*, *Cryptococcus neoformans*, *C. albicans*, *C. tropicalis*, *C. stellatoidea*, *C. glabrata*, *C. krusei*, *C. parapsilosis*, *C. guilliermondii*, *C. viswanathii*, *C. lusitaniae*, *Candida glabrata*, *Zygosaccharomyces*, and *Rhodoturola mucilaginosa*. It should be understood that the present methodologies are useful with any fungal organism that is resistant to antibiotics.

In certain embodiments, the target cells are bacterial cell strains. This list is not exhaustive as the disclosed methods can be used with any bacterial strain. Exemplary bacterial strains include, but are not limited to, strains from *Escherichia coli*, *Salmonella enterica*, *Streptomyces cinnamonensis*, *Streptomyces avermitilis*, *Staphylococcus aureus*, *Clostridium tetanomorphum*, *Clostridium tetani*, and *Helicobacter pylori*. In some aspects, each population of bacterial cell strains is resistant to one or more compounds known to suppress the growth of bacterial cell strains that are sensitive to the one or more compounds. It should be understood that the present methodologies are useful with any bacterial organism that is resistant to antibiotics.

Additionally, bacterial strains resistant to antibiotics can be generated using techniques known in the art. For instance, antibiotic resistant bacteria can be generated by blocking mismatch repair in a bacterium to make hypermutable bacteria, contacting the bacteria with at least one antibiotic, selecting bacteria that are resistant to the antibiotic, and culturing the antibiotic resistant bacteria. Such techniques are disclosed in United States Patent Publication No. 20030068808. Another technique involves transforming bacterial cells with PCR products homologous to gene sequences responsible for antibiotic sensitivity in the bacterial chromosome (see, e.g., Martin-Galiano and de la Campa, *Antimicrob Agents Chemother.* 47(4): 1257-1261 (2003)). Furthermore, antibiotic resistant bacteria can be generated by exposing the bacterial cells to an antibiotic and determining those cells that survive.

In other embodiments, the target cells are strains of cancer cells. In further embodiments, each population of cancer cells is resistant to one or more compounds known to suppress the growth of cancer cells sensitive to the one or more compounds. Any cancer cells can be used in the disclosed methods. Non-limiting exemplary cancer cells include strains of small cell lung cancer cells, non-small cell lung cancer cells, stomach cancer cells, colon cancer cells, bone cancer cells, brain cancer cells, breast cancer cells, and adenocarcinomal cells. It should be understood that the present methodologies are useful with any cancer cell that develops resistance to anti-cancer agents.

In additional embodiments, the target cells can be strains of inflammatory cells. Any cells that mediate an inflammatory response can be used in the presently disclosed methods so long as such cells are the target of anti-inflammatory therapy. Exemplary strains of inflammatory cells include granulocytes, mast cells, basophils, T-cells, natural killer cells, leukocytes, and macrophages. It should be understood that the present methodologies are useful with any cells that develop resistance to agents that inhibit growth or kill the targeted cells.

The methods also provide for contacting the plurality of populations of target cells with a candidate compound and for the screening of compounds for a desired property such as antimicrobial, anti-inflammatory, or anti-cancer properties. As used herein, the term "candidate compound" means a compound that is being tested for its ability to suppress the growth of a target cell. The candidate compound can be in an extract from a plant tissue, bacterial cells, fungal cells, or invertebrate tissues. Such extracts would be a complex mixture of molecules. In certain embodiments, the candidate compound is not identified from the complex mixture prior to testing for activity. In certain embodiments, the candidate compound is isolated from a complex mixture prior to testing for activity. In other embodiments, the candidate compound is synthesized prior to testing for activity. In some embodiments, the one or more compounds are antimicrobial compounds. In some embodiments, these antimicrobial compounds are antibiotics. In others, these antimicrobial compounds are anti-fungal agents. In some cases, the one or more compounds are anti-cancer or anti-inflammatory agents.

Furthermore, the one or more compounds can be isolated from an extract. The extract can be isolated from a bacterial organism, an invertebrate organism (including single-celled organisms), a fungal organism, or a plant tissue. The origin of the novel compounds is not important so long as an investigator can determine whether the extract inhibited or suppressed the growth of the target cell. For example, a plant tissue can be homogenized to yield a cellular homogenate and the homogenate can be provided to the panel of cells to determine whether it inhibits the growth of all of the target cells in the panel. If such growth is inhibited, then the homogenate has a unique, previously unknown compound or compounds that inhibits the growth of the target cells. The homogenate can then be analyzed to identify and isolate the compound or compounds that exhibit the growth inhibiting effect. In some instances, a candidate compound is isolated from a bacterial organism, a fungal organism, an invertebrate organism, or a plant tissue prior to contacting the panel of target cells. In some cases, a candidate compound is made using standard chemical techniques rather than being isolated or extracted from cells or tissues.

An example of how agents exhibiting growth inhibition or suppression characteristics is provided herein. In this example, a panel of microbial strains collectively resistant to all or most of known antimicrobials allow for efficient screening for novel chemical antibiotics. In this example, there are approximately 5000 antibiotics discovered to date, and a panel of 5000 strains of Staphylococcus aureus, each of which is resistant to one known antibiotic can be used to select of an unknown, previously undescribed antibiotic. However, the number of resistant strains used to screen for new antibiotics can be varied across any number of strains, depending on the number of different resistant strains that are known or identified. It should be noted that every known strain of Staphylococcus aureus can be used to identify new antibiotics. Once the panel of bacteria are identified, a test source of candidate molecules is applied to the panel. In this example, the test source is from a bacterial culture. However, the test source of candidate molecules can be an extract of a microbial culture, fungal culture, plant/invertebrate tissue, or a sample from the environment. In addition, the candidate molecules can be purified prior to being applied to the panel or can be made by known chemical techniques. Furthermore, the compound may be part of a chemical library. Such compounds are typically synthesized or purified.

Returning to the example, the investigator determines whether the growth of the Staphylococcus strains have been inhibited by the test source. This determination is performed by identifying cell growth. Methods of identifying cell growth include visually identifying growing cells using light microscopy. Furthermore, optical detection of cell proliferation can be performed using known techniques such as the CytoSelect™ Cell Viability and Cytotoxicity Assay Kit commercially available through Cell Bio Labs, Inc. (San Diego, Calif.). In addition, detecting single cells in a sample has been discussed by Tanyeri and Kennedy, (2008) *Sens Lett.* 6(2): 326-329; the disclosure of which is incorporated by reference.

EXAMPLE

Example 1

In a small scale experiment, ten strains of Staphylococcus aureus, each resistant to a different, known, antibiotic, were generated. These strains were added to the wells of a microplate. When these ten known antibiotics were separately added to the wells containing the ten resistant strains, at least some of the wells exhibited microbial growth. Thus, it was determined that each strain of Staphylococcus aureus was resistant to at least one of ten known antibiotics (FIG. 1).

A different antibiotic was applied (linezolid) and suppressed the growth in all the wells (FIG. 1). In this way, it was shown that linezolid was not part of the initial set of ten antibiotics. In other words, the panel of ten Staphylococcus aureus strains used allowed dereplication of the ten antibiotics with no need for analytical chemistry. This experiment establishes that the panel of ten strains can be scaled up to several thousand strains, which will be collectively resistant to as many known antibiotics, and screen sources of unknown compounds (e.g., microbial or eukaryotic cell spent media, cell and tissue extracts, combinatorial libraries, etc.). Using such a large scale screen allows identification of a source containing an antimicrobial activity that is unique from the thousands of known antibiotics, and thus a likely source of a novel antibiotic. Similarly, and using either microbial spent media or individual compounds from chemical libraries, a search can be performed for novel compounds with anticancer, anti-inflammatory, or other desired properties.

Example 2

1. Production of Resistant Strains

Four strains from NARSA (Network on Antimicrobial Resistance in Staphylococcus aureus) could be purchased. The strains NRS106, NRS107, NRS128 and NRS129 show resistances against the antibiotics gentamicin, mupirocin, erythromycin and chloramphenicol.

The majority of mutants were obtained by selection of the S. aureus strain RN4220 on agar plates in presence of an antibiotic. Briefly, the minimal inhibitory concentration ("MIC") of the wildtype strain RN4220 was determined. For this purpose a liquid culture with an OD of 0.5 was added as a dilution of 1:100 in Mueller-Hinton broth to each well of a 96-well plate containing a dilution series of a certain antibiotic. The 96-well plate was incubated at 37° C. overnight. The lowest antibiotic concentration where no growth of bacteria could be determined is defined as the MIC value of this strain.

To select first-step mutants agar plates containing an antibiotic concentration of 0.5×-, 1×-, 2×-, 3×- and 5×MIC were prepared and approximately $1 \times 10^8$ cells were plated and incubated overnight. Colonies grown on the plate with the highest antibiotic concentration were subcultured in liquid MH-media containing the same concentration of antibiotic to avoid loss of resistance. This culture was used to prepare a 25% glycerol stock that is stored at −80° C. To test the stability of resistance each strain was subcultured again either in presence of an antibiotic or in media without any antibiotics. After that both cultures were plated on agar plates. In case of a stable mutation that leads to the resistance no difference in growth behavior of the liquid culture or the cultures plated on agar plates should be noticed. The MIC of the mutants was determined.

After the successful selection of eight first-step mutants the experiment was repeated in a same manner as described above to obtain mutants having a resistance to much higher concentration of antibiotic. With the exception of the actinomycin D mutant, additional mutants were obtained. Again the MIC-values for the new mutants were determined.

Table 1 shows the results of generating mutants using the above-described procedure. In particular, Table 1 shows the increased MIC for mutants generated by the methodology disclosed herein. Table 2 shows the mutants purchased from NARSA.

TABLE 1

Mutants Obtained By Selection

| Antibiotic to which the mutant is resistant | MIC of wildtype RN4220 [µg/ml] | MIC of the mutant [µg/ml] | Concentration at which the mutant was selected as a multiple of the MIC-value |
|---|---|---|---|
| Actinomycin D | 1.56 | 12.48 | 2×MIC |
| Ampicillin | 0.2 | 300 | 5×MIC |
| Novobiocin | 0.05 | 12.5 | 7×MIC |
| Ofloxacin | 0.4 | 1.5 | 5×MIC |
| Rifampicin | 0.008 | 250 | 382×MIC |
| Streptomycin | 25 | couldn't be determined | 5×MIC |
| Tetracyclin | 0.1 | 3.9 | 4×MIC |
| Vancomycin | 1.56 | 2000 | 19×MIC |

TABLE 2

Mutants Purchased From NARSA

| Antibiotic to which the mutant is resistant | MIC of wildtype RN4220 [µg/ml] | MIC of the mutant [µg/ml] |
|---|---|---|
| NRS106 Gentamicin | 250 | 0.8 |
| NRS107 Mupirocin | 500 | 25 |
| NRS128 Erythromycin | couldn't be determined | 0.8 |
| NRS129 Chloramphenicol | 62.5 | 12.5 |

2. Identification of Antibiotic-Resistant Bacteria

Linezolid was added as an antibiotic to each resistant strain and was expected to kill all strains because no mutant resistant to linezolid was selected. The experiment was performed in 96-well plates with one well that doesn't contain any antibiotic as a positive control and the wild-type strain RN4220 was tested against each antibiotic as a negative control. The bacteria cultures were added as a 1:100 dilution in fresh media when the OD reached a value of 0.5.

Figure 2:
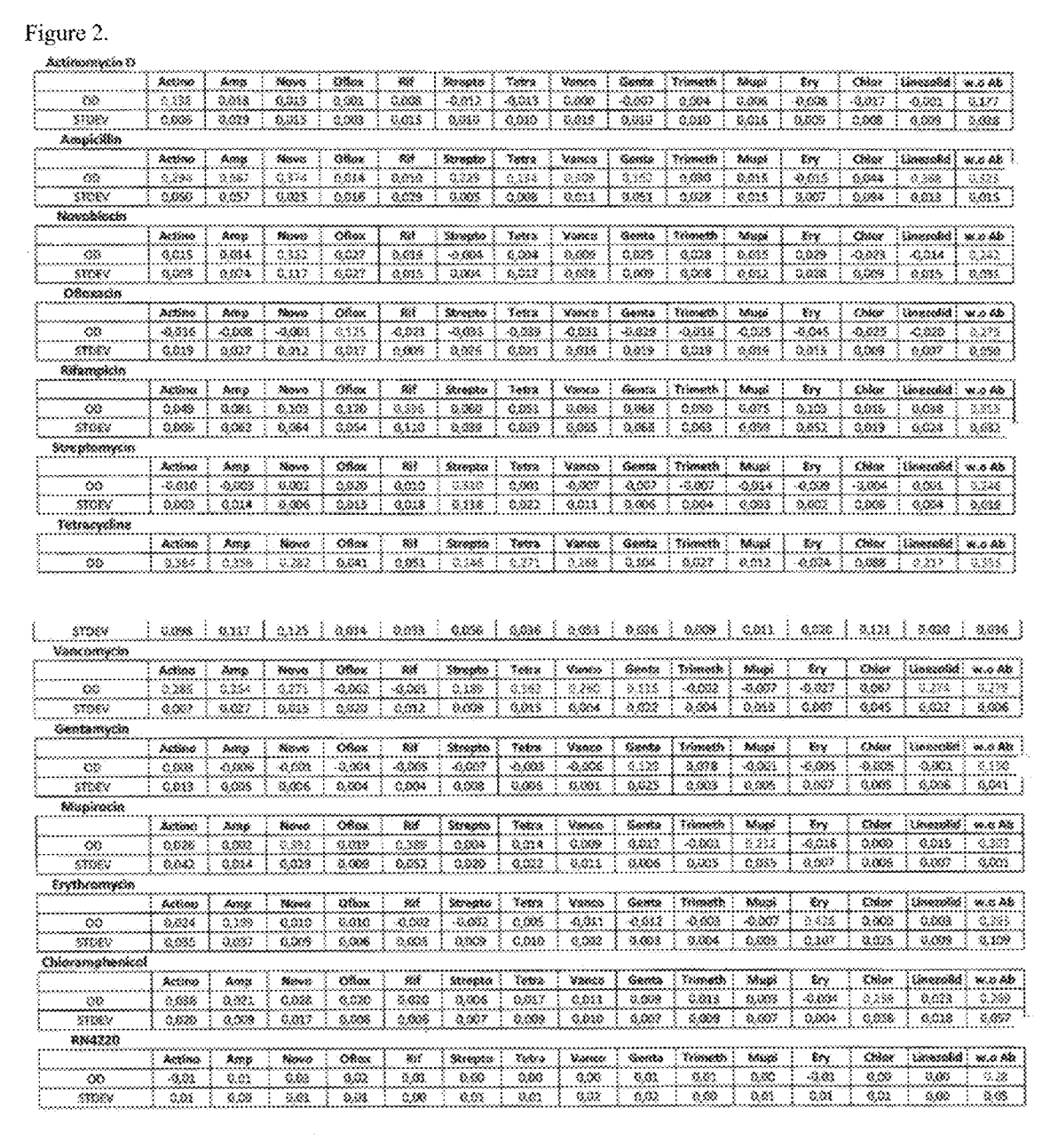

Table 3 shows the results of the experiment. In particular, strains were resistant to one or more antibiotics, as shown by "V," which designates growth of the cells. These results are also shown in FIG. 2. FIG. 2 shows the OD of mutant strains in each antibiotic. In addition, the strains were grown in the absence of antibiotics and their optical density is shown. It is apparent from FIG. 2 and Table 3 that each mutant was resistant to one or more antibiotics.

TABLE 3

Growth of Strains In Each Antibiotic

|     | Act | Amp | Nov | Ofl | Rif | Str | Tet | Van | Gen | Tri | Mup | Ery | Chl | Lin | w.o Ab |
|-----|-----|-----|-----|-----|-----|-----|-----|-----|-----|-----|-----|-----|-----|-----|--------|
| Act | V   | —   | —   | —   | —   | —   | —   | —   | —   | —   | —   | —   | —   | —   | V      |
| Amp | V   | V   | V   | —   | —   | V   | V   | V   | V   | —   | —   | —   | —   | V   | V      |
| Nov | —   | —   | V   | —   | —   | —   | —   | —   | —   | —   | —   | —   | —   | —   | V      |
| Ofl | —   | —   | —   | V   | —   | —   | —   | —   | —   | —   | —   | —   | —   | —   | V      |
| Rif | —   | —   | —   | —   | V   | —   | —   | —   | —   | —   | —   | —   | —   | —   | V      |
| Str | —   | —   | —   | —   | —   | V   | —   | —   | —   | —   | —   | —   | —   | —   | V      |
| Tet | V   | V   | V   | —   | —   | V   | V   | V   | —   | —   | —   | —   | —   | V   | V      |
| Van | V   | V   | V   | —   | —   | V   | V   | V   | V   | —   | —   | —   | —   | V   | V      |
| Gen | —   | —   | —   | —   | —   | —   | —   | —   | V   | —   | —   | —   | —   | —   | V      |
| Mup | —   | —   | V   | —   | V   | —   | —   | —   | —   | —   | V   | —   | —   | —   | V      |
| Ery | —   | V   | —   | —   | —   | —   | —   | —   | —   | —   | —   | V   | —   | —   | V      |
| Chl | —   | —   | —   | —   | —   | —   | —   | —   | —   | —   | —   | —   | V   | —   | V      |
| RN  | —   | —   | —   | —   | —   | —   | —   | —   | —   | —   | —   | —   | —   | —   | V      |

Act: Atinomycin D;
Amp: Ampicillin;
Nov: Novobiocin;
Ofl: Ofloxacin;
Rif: Rifampicin;
Str: Streptomycin;
Tet: Tetracycline;
Van: Vancomycin;
Gen: Gentamycin;
Tri: Trimethoprim;
Mup: Mupirocin;
Ery: Erythromycin;
Chl: Chloramphenicol;
Lin: Linezolid;
w.o. Ab: without antibiotic [positive control];
RN: RN4220 wildtype strain as negative control

The invention claimed is:

1. A method of identifying compounds that suppress the growth of target cells comprising:
   providing a panel of target cells, wherein the panel of target cells comprises a plurality of different populations of target cells, each population of target cells is resistant to different one or more compounds known to suppress the growth of cells sensitive to the one or more compounds;
   growing each population of target cells in the presence of a candidate compound;
   determining whether the candidate compound suppresses the growth of one or more populations of target cells; and
   selecting the candidate compound that suppresses the growth of all the different compound-resistant populations of target cells in the panel; wherein
   the candidate compound is in or obtained from an extract from a bacterial organism, an extract from an invertebrate organism, an extract from a fungal organism, an extract from a plant tissue, or
   a microbial spent medium.

2. The method of claim 1, wherein each population of target cells is a strain of bacteria.

3. The method of claim 1, wherein each population of target cells is a fungal strain.

4. The method of claim 1, wherein each population of target cells is a *Saccharomyces cerevisiae* strain.

5. The method of claim 4, wherein each population of *Saccharomyces cerevisiae* strains is resistant to one or more compounds known to suppress the growth of *Saccharomyces cerevisiae* strains sensitive to the one or more compounds.

6. The method of claim 1, wherein each population of target cells is a *Schizosaccharomyces pombe* strain.

7. The method of claim 4, wherein each population of *Schizosaccharomyces pombe* strains is resistant to one or more compounds known to suppress the growth of *Schizosaccharomyces pombe* strains sensitive to the one or more compounds.

8. The method of claim 1, wherein each population of target cells is an *Escherichia coli* strain.

9. The method of claim 8, wherein each population of *Escherichia coli* strains is resistant to one or more compounds known to suppress the growth of *Escherichia coli* strains sensitive to the one or more compounds.

10. The method of claim 2, wherein the one or more compounds are antibiotics.

11. The method of claim 3, wherein the one or more antimicrobial compounds are anti-fungal agents.

12. The method of claim 1, wherein contacting the plurality of populations of target cells with a candidate compound comprises contacting the plurality of populations with an extract from a bacterial organism, an extract from an invertebrate organism, an extract from a fungal organism, or an extract from a plant tissue.

13. The method of claim 1, wherein contacting the plurality of populations of target cells with a candidate compound comprises contacting the plurality of populations with a candidate compound isolated from a bacterial organism, a fungal organism, an invertebrate organism, or a plant tissue.

14. The method of claim 1, wherein the target cells are cancer cells.

15. The method of claim 14, wherein each population of cancer cells is resistant to one or more compounds known to suppress the growth of cancer cells sensitive to the one or more compounds.

16. The method of claim 14, wherein contacting the plurality of populations of target cells with a candidate compound comprises contacting the plurality of populations with a candidate compound isolated from a bacterial organism, a fungal organism, an invertebrate organism, or a plant tissue.

17. The method of claim 14, wherein contacting the plurality of populations of target cells with a candidate compound comprises contacting the plurality of populations with an extract from a bacterial organism, an extract from a fungal organism, an extract from an invertebrate organism, or an extract from a plant tissue.

18. The method of claim 1, wherein the target cells are cells that mediate inflammation.

19. The method of claim 18, wherein each population of cells that mediate inflammation is resistant to one or more compounds known to suppress the growth of cells that mediate inflammation.

20. The method of claim 18, wherein contacting the plurality of populations of target cells with a candidate compound comprises contacting the plurality of populations with a candidate compound isolated from a bacterial organism, a fungal organism, an invertebrate organism, or a plant tissue.

21. The method of claim 18, wherein contacting the plurality of populations of target cells with a candidate compound comprises contacting the plurality of populations with an extract from a bacterial organism, an extract from a fungal organism, an extract from an invertebrate organism, or an extract from a plant tissue.

22. The method of claim 1, wherein the candidate compounds kill each of the plurality of populations of target cells.

23. The method of claim 14, wherein the candidate compound exhibits anti-cancer activity.

24. The method of claim 18, wherein the candidate compound exhibits anti-inflammatory activity.

25. The method of claim 1, wherein the plurality of populations of target cells is provided in a multiwell plate.

26. The method of claim 1, wherein the panel comprises at least 100 populations of target cells.

27. The method of claim 1, wherein the candidate compound is obtained from a microbial spent medium.

28. The method of claim 1, wherein the candidate compound is obtained from a chemical library.

29. The method of claim 18, wherein the cells that mediate inflammation are selected from the group consisting of granulocytes, mast cells, basophils, T-cells, natural killer cells, leukocytes, and macrophages.

30. The method of claim 1, wherein the determining whether the candidate compound suppresses the growth of one or more populations of target cells is carried out using spectrophotometry, flow cytometry, luminosity assay, colorimetric assay, or fluorescence assay.

\* \* \* \* \*